US009012626B2

(12) United States Patent
Prakash et al.

(10) Patent No.: US 9,012,626 B2
(45) Date of Patent: *Apr. 21, 2015

(54) REBAUDIOSIDE A COMPOSITION AND METHOD FOR PURIFYING REBAUDIOSIDE A (75) Inventors: Indra Prakash, Alpharetta, GA (US);
Mani Upreti, Dunwoody, GA (US);
Grant E. DuBois, Roswell, GA (US);
George A. King, Atlanta, GA (US);
Anish Mehta, Alpharetta, GA (US)

(73) Assignee: The Coca-Cola Company, Atlanta, GA (US)

( * ) Notice: Subject to any disclaimer, the term of this patent is extended or adjusted under 35 U.S.C. 154(b) by 569 days.

This patent is subject to a terminal disclaimer.

(21) Appl. No.: 12/650,637

(22) Filed: Dec. 31, 2009

(65) Prior Publication Data
US 2010/0137569 A1 Jun. 3, 2010

Related U.S. Application Data (63) Continuation-in-part of application No. 11/751,627, filed on May 21, 2007.

(60) Provisional application No. 60/805,216, filed on Jun. 19, 2006, provisional application No. 60/889,318, filed on Feb. 12, 2007.

(51) Int. Cl.
C07H 1/06 (2006.01)
C07H 1/08 (2006.01)
C07H 15/256 (2006.01)
A23L 1/236 (2006.01)

(52) U.S. Cl.
CPC .............. C07H 1/08 (2013.01); A23L 1/2366 (2013.01); A23V 2002/00 (2013.01); C07H 15/256 (2013.01)

(58) Field of Classification Search
CPC ...... C07H 1/08; C07H 15/256; A23L 1/2366; A23V 2002/00
See application file for complete search history.

(56) References Cited

U.S. PATENT DOCUMENTS

| 3,723,410 | A | 3/1973 | Persinos |
| 4,082,858 | A | 4/1978 | Morita et al. |
| 4,188,390 | A | 2/1980 | Campbell et al. |
| 4,206,222 | A | 6/1980 | Valetas et al. |
| 4,219,571 | A | 8/1980 | Miyake |
| 4,332,830 | A | 6/1982 | DuBois |
| 4,353,889 | A | 10/1982 | DuBois |
| 4,361,697 | A | 11/1982 | Dobberstein et al. |
| 4,381,402 | A | 4/1983 | DuBois |
| 4,402,990 | A | 9/1983 | DuBois |
| 4,404,367 | A | 9/1983 | DuBois |
| 4,454,290 | A | 6/1984 | DuBois |
| 4,515,785 | A | 5/1985 | Shimizu et al. |
| 4,590,160 | A | 5/1986 | Nishihashi et al. |
| 4,599,403 | A | 7/1986 | Kumar |
| 5,112,610 | A | 5/1992 | Kienie |
| 5,530,106 | A | 6/1996 | Navia et al. |
| PP10,562 | P | 8/1998 | Sys et al. |
| PP10,563 | P | 8/1998 | Brandle et al. |
| PP10,564 | P | 8/1998 | Marsolais et al. |
| 5,962,678 | A | 10/1999 | Payzant et al. |
| 5,972,120 | A | 10/1999 | Kutowy et al. |
| 6,255,557 | B1 | 7/2001 | Brandle |
| 6,331,646 | B1 | 12/2001 | Schroeder et al. |
| 6,423,864 | B1 | 7/2002 | Prakash et al. |
| 6,784,309 | B2 | 8/2004 | Prakash et al. |
| 6,809,198 | B2 | 10/2004 | El Kabbani et al. |
| 6,998,480 | B2 | 2/2006 | Catani et al. |
| 7,049,435 | B2 | 5/2006 | Catani et al. |
| 2002/0065245 | A1 | 5/2002 | Brouwers |
| 2003/0138538 | A1 | 7/2003 | Kitazume et al. |
| 2004/0030124 | A1 | 2/2004 | Catani et al. |
| 2005/0010040 | A1 | 1/2005 | Gourdin et al. |
| 2006/0083838 | A1 | 4/2006 | Jackson et al. |
| 2006/0134292 | A1 | 6/2006 | Abelyan et al. |
| 2006/0142555 | A1 | 6/2006 | Jonnala et al. |
| 2007/0082102 | A1 | 4/2007 | Magomet et al. |
| 2007/0082103 | A1 | 4/2007 | Magomet et al. |
| 2007/0116800 | A1 | 5/2007 | Prakash et al. |
| 2007/0116819 | A1 | 5/2007 | Prakash et al. |
| 2007/0116820 | A1 | 5/2007 | Prakash et al. |

(Continued)

FOREIGN PATENT DOCUMENTS

CA 2278083 1/2001
EP 1407679 4/2004

(Continued)

OTHER PUBLICATIONS

"Recrystallization Guide" by Organic Chemistry Help! [online] [Retrieved on Jan. 30, 2013] Retrieved from the internet at <http://www.chemhelper.com/recryst.html> Published online Mar. 8, 2006.*

(Continued)

Primary Examiner — Scarlett Goon
(74) Attorney, Agent, or Firm — King & Spalding (57) ABSTRACT Exemplary embodiments of this invention encompass a method for purifying a low purity steviol glycoside composition. In particular, this invention relates to a method for purifying low purity steviol glycoside compositions to obtain substantially pure steviol glycoside compositions comprising approximately 95% or greater steviol glycosides and approximately 75% or greater rebaudioside A with a single crystallization step.

13 Claims, 1 Drawing Sheet

(56) References Cited

U.S. PATENT DOCUMENTS

| | | |
|---|---|---|
| 2007/0116821 A1 | 5/2007 | Prakash et al. |
| 2007/0116822 A1 | 5/2007 | Prakash et al. |
| 2007/0116823 A1 | 5/2007 | Prakash et al. |
| 2007/0116824 A1 | 5/2007 | Prakash et al. |
| 2007/0116825 A1 | 5/2007 | Prakash et al. |
| 2007/0116826 A1 | 5/2007 | Prakash et al. |
| 2007/0116827 A1 | 5/2007 | Prakash et al. |
| 2007/0116828 A1 | 5/2007 | Prakash et al. |
| 2007/0116829 A1 | 5/2007 | Prakash et al. |
| 2007/0116830 A1 | 5/2007 | Prakash et al. |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0128311 A1 | 6/2007 | Prakash et al. |
| 2007/0134390 A1 | 6/2007 | Prakash et al. |
| 2007/0134391 A1 | 6/2007 | Prakash et al. |
| 2007/0292582 A1* | 12/2007 | Prakash et al. ............... 426/548 |
| 2010/0137569 A1 | 6/2010 | Prakash et al. |

FOREIGN PATENT DOCUMENTS

| | | |
|---|---|---|
| JP | 52062300 | 5/1977 |
| JP | 56121453 | 9/1981 |
| JP | 56121455 | 9/1981 |
| JP | 57086264 A | 5/1982 |
| JP | 59071662 A | 4/1984 |
| JP | 59120073 A | 7/1984 |
| JP | 60027360 A | 2/1985 |
| JP | 60037950 A | 2/1985 |
| JP | 62091161 A | 4/1985 |
| WO | WO 0032621 | 6/2000 |
| WO | WO 0052019 | 9/2000 |
| WO | WO 2006038221 | 4/2006 |
| WO | WO 2007149672 A2 | 12/2007 |

OTHER PUBLICATIONS

"2.2 Recrystalllization" [online], retrieved Dec. 10, 2009, published on the internet Sep. 12, 2003. <http://siggy.chem.ucla.edu/VOH/136/Recrystallization.pdf>.

Boggan, B., "Alcohol, Chemistry, and You," online from ChemCases. Com Edition (retrieved Oct. 18, 2010), available Oct. 3, 2011.

Bonomelli, Federico, "International Search Report and Written Opinion of the International Searching Authority", Oct. 14, 2008, PCT/US2008/063845, European Patent Office, Rijswijk, The Netherlands.

Hancock, B.C. and Parks, M., "What is the True Solubility Advantage for Amorphous Pharmaceuticals," *Pharmaceuticals Research* vol. 17, No. 4, pp. 397-404 (2000).

Kojima, S. "ICH Guideline for Residual Solvents (Q3C)," Proceedings of the 4th International Conference on Harmonization of Technical Requirements for Registration of Pharmaceuticals, online (retrieved Apr. 2, 2010), Brussels, Belgium Jul. 16-18, 1997.

Kolai, P. et al. "Solvent selection for pharmaceuticals" *Fluid Phase Equilibria*, vol. 194-197, p. 771-782 (2002).

Lombart, Isabelle, "International Search Report and Written Opinion of the International Searching Authority", Mar. 22, 2011, PCT/US2010/062479, European Patent Office, Rijswijk, The Netherlands.

Longo, Eleonora, "International Search Report and Written Opinion of the International Searching Authority", May 23, 2007, PCT/US2007/069548, European Patent Office, Rijswijk, The Netherlands.

Luft, J.R., et al., "Efficient optimization of crystallization conditions by manipulation of drop volume and temperature," *Protein Science* vol. 16, No. 4, pp. 715-722 (2007).

Mullin, J.W., "Industrial Crystallization" in *Crystallization* , Butterworth Inc., pp. 158-169 (1961).

Nass, K.K., et al. "Rational Solvent Selection for Cooling Crystallizations" *Industrial & Engineering Chemistry Research*, vol. 33, p. 1580-1584 (1994).

PTI Process Chemicals, "Denatured Alcohol MSDS," online (retrieved Oct. 18, 2010), published Apr. 25, 2005.

Shibata et al. "Glucosylation of Steviol and Steviol-Glucosides in Extracts from *Stevia rebaudiana* Bertoni" *Plant Physiol.* vol. 95, p. 152-156 (1991).

Third Party Submission in related U.S. Appl. No. 11/751,627, received Jun. 26, 2012.

Zell. et al. Tetrahedron 56(36) 6603-6016 (2000).

* cited by examiner

REBAUDIOSIDE A COMPOSITION AND METHOD FOR PURIFYING REBAUDIOSIDE A

RELATED APPLICATION DATA

The present application is a continuation-in-part of U.S. patent application Ser. No. 11/751,627 filed in the U.S. Patent and Trademark Office on May 21, 2007, which claims priority under 35 U.S.C. §119(e) to U.S. Provisional Application Ser. Nos. 60/805,216, filed on Jun. 19, 2006, and 60/889,318, filed on Feb. 12, 2007, each entitled "Rebaudioside A Composition and Method for Purifying Rebaudioside A." The disclosures of these applications are hereby incorporated by reference in their entirety.

FIELD OF INVENTION

This invention relates generally to methods for purifying low purity steviol glycoside compositions to obtain substantially pure steviol glycoside compositions at a high yield. In another aspect, this invention relates to methods for purifying low purity rebaudioside A and low purity steviol glycoside compositions to obtain substantially pure steviol glycoside compositions having acceptable levels of rebaudioside A at a high yield.

BACKGROUND OF INVENTION

Rebaudioside A is a high-potency diterpenoid glycoside sweetener having the chemical structure:

Rebaudioside A is isolated and extracted, along with other steviol glycosides, from the *Stevia rebandiana* (Bertoni) plant ("*Stevia*"), which is commercially cultivated in Japan, Singapore, Taiwan, Malaysia, South Korea, China, Israel, India, Brazil, Australia, and Paraguay. It is an alternative non-caloric sweetener with functional and sensory properties superior to those of many high-potency sweeteners. Processed forms of *Stevia* can be 3 to 300 times more potent than sugar; however, *Stevia* also has a bitter component. Of the four major diterpenoid glycoside sweeteners present in *Stevia*, rebaudioside A has been identified as the least bitter, and with the least persistent aftertaste. Bitterness often is significantly due to the impurities in extracts.

Current Joint FAO/WHO Expert Committee on Food Additives (JECFA) standards require that the total amount of steviol glycosides be purified to 95% or greater. Compositions of steviol glycosides currently are only available having from 80-92 steviol glycosides by weight—with the cost of these compositions increasing substantially as the purity levels of the steviol glycosides and/or rebaudioside A are increased. In addition, these compositions generally fail to provide sufficient purities of rebaudioside A among the steviol glycosides (e.g., generally having only ≤80% rebaudioside A by weight).

Previously reported efforts to purify rebaudioside A from mixtures of rebaudioside A and stevioside require numerous repeated purification steps. U.S. Pat. No. 5,962,678 discloses the re-crystallization of rebaudioside A using an anhydrous methanol solution to obtain an 80% pure rebaudioside A. By repeating the re-crystallization with anhydrous methanol numerous times, the purity of rebaudioside A may be increased to over 95%. U.S. Patent Publication No. 2006/0083838 discloses purification of rebaudioside A through re-crystallization with a solvent comprising ethanol and between 4 and 15% water. Japanese Patent Application No. 55-23756 discloses a method for purifying rebaudioside A and stevioside by crystallization from aqueous ethanol (>70%) to obtain an 80% pure rebaudioside A. U.S. Patent Publication No. 2007/0082103 discloses a method for purifying rebaudioside A by recrystallization from aqueous ethanol, asserting a two-step recrystallization from crude rebaudioside (60%) results in the formation of >98% pure rebaudioside at 97% yield. These prior art methods, however, do not provide a substantially pure steviol glycoside composition nor a rebaudioside A compositions of sufficient purity using only a single recrystallization step which is capable of satisfying current JECFA standards.

Accordingly, there exists a need for a simple, efficient, and economical method for preparing substantially pure steviol glycoside and rebaudioside A compositions.

SUMMARY OF INVENTION

Exemplary embodiments of the invention address the above-identified need by providing methods for purifying a low purity steviol glycoside composition to obtain a substantially pure steviol glycoside compositions having a high purity with a high yield.

In a particular embodiment, the method for purifying a low purity steviol glycoside composition comprises a simple crystallization. In particular, the method comprises combining a low purity steviol glycoside A composition and an organic solvent to form a steviol glycoside solution, the low purity steviol glycoside composition comprising up to 92% total steviol glycosides on a dry basis, and thereafter crystallizing from the low purity steviol glycoside solution in a single step a substantially pure steviol glycoside composition comprising rebaudioside A and one or more other steviol glycosides selected from the group consisting of rebaudioside B, rebaudioside C, rebaudioside D, rebaudioside F, rebaudioside F, stevioside, dulcoside A, rubusoside, and steviolbioside. The steviol glycosides are present in the substantially pure steviol glycoside composition in an amount of 95% or greater by weight on a dry basis. In an embodiment, the rebaudioside A is present in the substantially pure steviol glycoside composition in an amount of 75% or greater by weight on a dry basis. The total mass yield of the substantially pure steviol glycoside composition is 25% or greater by weight.

Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

DETAILED DESCRIPTION OF INVENTION

Steviol glycoside compositions may be used as natural high-potency sweeteners. Rebaudioside A is one of the steviol glycosides that may be found in varying amounts in steviol glycoside compositions. As the amount of the total steviol glycosides (including rebaudioside A) is increased, the cost of the composition also is increased substantially. Similarly, as the amount of rebaudioside A in the steviol glycoside compositions is increased, the cost of the composition is still further increased.

In U.S. patent application Ser. No. 11/751,627, Applicants' disclosed simple and economic methods for preparing substantially pure rebaudioside A compositions suitable for use as a natural high-potency sweetener. The phrase "substantially pure rebaudioside A" was used to refer to rebaudioside A compositions including at least about 85% by dry weight rebaudioside A, at least about 90% by dry, weight rebaudioside A, from about 95% to about 98% by dry weight rebaudioside A, and from about 99% to about 100% by dry weight rebaudioside A.

Applicants' have now discovered that the sweet taste and quality of these natural high-potency sweetener compositions not only is impacted by the amount of rebaudioside A present in the composition, but also by the total combined amount of steviol glycosides present in the composition. Accordingly, there exists a need to provide a method for preparing substantially pure steviol glycoside compositions in an economic manner. In particular, there exists a need to provide a method for preparing substantially pure steviol glycoside compositions having a high purity of rebaudioside A in an economic manner.

Exemplary embodiments of this invention satisfy these needs by providing a method for purifying a low purity steviol glycoside composition to a substantially pure steviol glycoside composition. The make-up and yield of the resulting substantially pure steviol glycoside composition may be controlled through the appropriate selection of parameters such as the type and amount of organic solvent, the solution temperature, the precipitation temperature, the mixing time, the precipitation time, and seeding of the solution.

The method generally comprises crystallization of a substantially pure steviol glycoside composition from a low purity steviol glycoside composition and an organic solvent in a single step. Other exemplary embodiments of this invention encompass a substantially pure steviol glycoside composition comprising a high purity of rebaudioside A.

Method of Purifying Low Purity Steviol Glycoside Compositions

Low purity steviol glycoside compositions are commercially available comprising steviol glycosides in purities up to about 92% by weight. As used herein, a "crude steviol glycoside composition" and a "low purity steviol glycoside composition" are used interchangeably to refer to compositions comprising steviol glycosides in amounts from about 80 to about 92% by weight.

In particular embodiments, the low purity steviol glycoside composition comprises up to about 60% rebaudioside A by weight on a dry basis. As used herein, a "crude rebaudioside A composition" or a "low purity rebaudioside A composition" are used interchangeably to refer to compositions comprising rebaudioside A in amounts from about 15% to about 60% by weight, about 30% to about 60% by weight, or about 40% to about 60% by weight. The remainder of the crude rebaudioside A composition generally comprises other steviol glycosides and impurities. Generally, commercially available low purity rebaudioside A compositions contain from about 80% to about 92% of steviol glycosides by weight.

It also is envisioned that low purity steviol glycoside compositions and crude rebaudioside A in its raw form, as extracted from *Stevia* plants, may be purified using the methods provided herein.

In an exemplary embodiment of purifying a low purity steviol glycoside composition, the low purity steviol glycoside composition may be combined with an organic solvent to form a low purity steviol glycoside solution. The organic solvent optionally may further comprise water in an amount up to about 25% by weight. For example, in particular embodiments the organic solvent may further comprise water in an amount from about 3% to about 20% by weight, from about 5% to about 15% by weight, from about 5% to about 10%, or any amounts therebetween. Non limiting examples of organic solvents include alcohol, acetone, acetonitrile, and ethyl acetate. Alcohol, as used herein, refers to any straight, branched, or cyclic; substituted or unsubstituted alkyl, alkenyl, or alkynyl group attached to at least one hydroxyl moiety. Non-limiting examples of alcohols include ethanol, methanol, isopropanol, 1-propanol, 1-butanol, 2-butanol, tert-butanol, and isobutanol.

In an exemplary embodiment, the organic solvent comprises a mixture of water and at least one organic solvent. In another exemplary embodiment, the at least one organic solvent comprises an alcohol, the alcohol comprising ethanol, methanol, or mixtures thereof. In exemplary embodiments wherein the at least one organic solvent comprises a mixture of ethanol and methanol, the ethanol and methanol may be combined in the organic solvent in a weight ratio ranging from about 20 parts to about 1 part ethanol to about 1 part methanol. In another exemplary embodiment, the ethanol and methanol may be combined in the organic solvent in a weight ratio ranging from about 3 parts to about 1 part ethanol to about 1 part methanol.

In an exemplary embodiment, the low purity steviol glycoside solution comprises the organic solvent and the low purity steviol glycoside composition in a weight ratio ranging from about 10 to about 4 parts organic solvent to about 1 part low purity steviol glycoside. In another exemplary embodiment, the low purity steviol glycoside solution comprises the organic solvent and the low purity steviol glycoside composition in a weight ratio ranging from about 5 to about 3 parts organic solvent to about 1 part low purity steviol glycoside.

The method of preparing the low purity steviol glycoside solution comprising the organic solvent and the low purity steviol glycoside composition may be carried out at any suitable temperature. Such temperatures generally may range from about 20° C. to about 85° C. For example, in an embodiment the low purity steviol glycoside solution may be prepared at approximately room temperature (approximately 22-25° C.). In another embodiment, the low purity steviol glycoside solution may be prepared by heating the steviol glycoside solution to a temperature in a range from about 20° C. to about 70° C., from about 20° C. to about 60° C., from about 20° C. to about 40° C., or from about 40° C. to about 60° C. In still another embodiment, the low purity steviol glycoside solution may be prepared by heating the low purity steviol glycoside solution to about reflux temperature (approximately 85° C.). The step of preparing (or mixing) the low purity steviol glycoside solution may be carried out for a length of time suitable to substantially suspend the low purity steviol glycoside in the organic solvent. For example, the low purity steviol glycoside solution may be prepared by mixing the low purity steviol glycoside solution for about 5 minutes to about 60 minutes, for about 5 to about 30 minutes, for about 10 to about 15 minutes, or for any length of time therebetween.

The method for purifying the low purity steviol glycoside composition further comprises crystallizing from the low purity steviol glycoside solution in a single step a substantially pure steviol glycoside composition comprising rebaudioside A. In particular embodiments, the crystallization of the low purity steviol glycoside solution may further comprise cooling the low purity steviol glycoside solution. Generally, the low purity steviol glycoside solution may be cooled to a temperature suitable for precipitation ("precipitation temperature") of the steviol glycosides and rebaudioside A from the low purity steviol glycoside solution. Non-limiting examples of such precipitation temperatures may be in a range from about 4° C. to about 35° C., from about 15° C. to about 25° C., or any temperature therebetween. Crystallization of the low purity steviol glycoside solution may be allowed to take place for a length of time sufficient ("precipitation time" or "cooling time") to obtain a desirable yield of the substantially pure steviol glycoside composition from the low purity steviol glycoside solution. For example, in particular embodiments the crystallization of the low purity steviol glycoside solution may proceed from about 0.5 hours to about 120 hours (5 days), about 12 hours to about 96 hours (4 days), about 24 hours (1 day) to about 72 hours (3 days), for about 48 hours (2 days), or for any length of time therebetween.

After crystallization of the low purity steviol glycoside solution, a substantially pure steviol glycoside composition may be obtained comprising rebaudioside A. A "substantially pure steviol glycoside composition" is used herein to refer to compositions comprising about 95% or greater by weight (on a dry basis) of steviol glycosides. The steviol glycosides may include rebaudioside A in combination with one or more other steviol glycosides selected from the group consisting of rebaudioside B, rebaudioside C, rebaudioside D, rebaudioside E, rebaudioside F, stevioside, steviolbioside, rubusoside, and dulcoside. In particular embodiments, the substantially pure steviol glycoside composition comprises rebaudioside A in an amount from about 70% or greater by weight. In particular embodiments, the substantially pure steviol glycoside composition further comprises rebaudioside B, rebaudioside C, rebaudioside D, rebaudioside F, stevioside, and steviolbioside. The substantially pure steviol glycoside composition generally comprises rebaudioside A in an amount of about 70% or greater by weight (on a dry basis), about 75% or greater by weight, about 80% or greater by weight, about 85% or greater by weight, about 90% or greater by weight, about 95% or greater by weight, or about 97% or greater by weight.

In particular embodiments, the total yield of the substantially pure steviol glycoside composition and the rebaudioside A may be about 25% or greater and about 20% or greater, respectively. Yield is used herein generally to refer to the mass obtained relative to the starting mass. Thus, the yield of the steviol glycosides may be determined by comparing the mass of the nine steviol glycosides in the substantially pure steviol glycoside composition as compared to the starting mass of the nine steviol glycosides in the low purity steviol glycoside. Similarly, the yield of the rebaudioside A composition may be determined by comparing the mass of rebaudioside A present in the substantially pure steviol glycoside composition as compared to the starting mass of the rebaudioside A present in the low purity steviol glycoside. In exemplary embodiments, the total yield of the substantially pure steviol glycoside composition and the rebaudioside A may be about 15% or greater, about 40% or greater, or about 60% or greater.

In an exemplary embodiment, the method of purifying the low purity steviol glycoside composition optionally may further comprise seeding the low purity steviol glycoside solution upon beginning the crystallization of the low purity steviol glycoside solution. Seeding generally may be performed at the same temperature at which the crystallization is allowed to proceed. For example, in particular embodiments the seeding will be conducted at temperatures in the range of about 18° C. to about 35° C. Seeding of the low purity steviol glycoside solution generally may be performed by adding substantially pure crystals of rebaudioside A to the low purity steviol glycoside solution in an amount sufficient to promote precipitation of the rebaudioside A and other steviol glycosides. An amount sufficient to promote precipitation generally may comprise a substantially pure rebaudioside A composition in an amount from about 0.0001% to about 1% by weight of the low purity steviol glycoside solution, from about 0.01% to about 1% by weight, or any amount therebetween.

In another exemplary embodiment, the method further comprises separating and washing the substantially pure steviol glycoside composition after its crystallization. The substantially pure steviol glycoside composition may be separated from its supernatant (the organic solvent and impurities) by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge. Heinkel type centrifuge, disc stack centrifuge and cyclone separation. Additionally, separation may be enhanced by any pressure, vacuum, or gravity filtration methods, that include without limitation, the use of belt, drum, nutsche type, leaf, plate, Rosenmund type, sparkler type, and bag filters and filter press. Operation of the solid-liquid separation device may be continuous, semi-continuous or in batch mode. The substantially pure steviol glycoside composition also may be washed on the separation device using various organic solvents and mixtures thereof and can be partially or totally dried on the separation device using any number of gases, including, without limitation, nitrogen or argon, to evaporate residual liquid solvent. The substantially pure steviol glycoside composition may be automatically or manually removed from the separation device using liquids, gases or mechanical means by either dissolving the solid or maintaining the solid form.

In still another exemplary embodiment, the method further comprises drying the substantially pure steviol glycoside composition. Suitable methods for drying such compositions are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the substantially pure steviol glycoside composition is dried using a nitrogen or argon purge to remove the residual solvent at a temperature in a range from about 40° C. to about 60° C. for a period of time from about 5 hours to about 5 days, from about 1 day to about 4 days, from about 2 days to about 3 days, or for any length of time therebetween.

If further purification is desired, the method of purifying the low purity steviol glycoside composition described herein may be repeated or the substantially pure steviol glycoside composition may be further purified using an alternative purification method, such as the column chromatography.

Purity, as used herein with respect to the steviol glycoside composition, represents the weight percentage of select steviol glycosides (e.g., rebaudioside A, rebaudioside B, rebaudioside C, rebaudioside D, rebaudioside E, rebaudioside F, stevioside, dulcoside A, rubusoside, and steviolbioside) in the steviol glycoside composition. Purity, as used herein with respect to the rebaudioside A, represents the weight percentage of rebaudioside A in the low purity steviol glycoside composition or substantially pure steviol glycoside composition. Accordingly, the substantially pure steviol glycoside compositions provided herein comprise rebaudioside A in a particular purity and the combined total of select steviol glycosides in a particular purity. The remainder of the composition may comprise impurities or other steviol glycosides present in amounts which are below detectable limits. Impurities or other steviol glycosides present in amounts less than about 0.1% of the total composition by weight are considered below the detectable limit.

The select steviol glycosides generally comprise one or more of steviol glycosides selected from the group consisting of rebaudioside A, rebaudioside B, rebaudioside C, rebaudioside D, rebaudioside F, stevioside, dulcoside A, rubusoside, and steviolbioside. For example, in one embodiment the total amount of the combined steviol glycosides is based on the combination of nine steviol glycosides—i.e., rebaudioside A, rebaudioside B, rebaudioside C, rebaudioside D, rebaudioside F, stevioside, dulcoside A, rubusoside, and steviolbioside. In another embodiment the combined total of steviol glycosides is based on the combination of seven steviol glycosides—i.e., rebaudioside A, rebaudioside B, rebaudioside C, rebaudioside D, rebaudioside F, stevioside, and steviolbioside. Those skilled in the art will appreciate that the steviol glycosides included within the combined total of steviol glycosides may be selected based on particular food regulations or recommendations set forth by various governing bodies (e.g., JECFA, United States Food and Drug Administration, etc.).

The purity of the composition may be measured using methods known to those of ordinary skill in the art. One such method includes high performance liquid chromatography (HPLC). Those of ordinary skill in the art also should appreciate that the moisture in the sample may affect the accuracy of purity measurements. Accordingly, the composition should be substantially dry when measured for purity. As used herein, a "substantially dry composition" and "on a dry basis" are used interchangeably and may comprise up to about 10% by weight of moisture.

Rebaudioside A Polymorphic and Amorphous Forms

As Applicants previously have described in U.S. patent application Ser. No. 11/751,627, the purification of rebaudioside A compositions may result in the formation of various polymorphic and amorphous forms of rebaudioside A. Applicants previously identified at least three different polymorphs of rebaudioside A: Form 1: a rebaudioside A hydrate; Form 2: an anhydrous rebaudioside A, and Form 3: a rebaudioside A solvate. In addition to the at least three polymorphic forms of rebaudioside A, Applicants also have identified an amorphous form of rebaudioside A, Form 4.

Polymorphism is defined as the ability of a substance to exist as two or more crystalline states that have different arrangements and/or conformations of the molecules in the crystal lattice. Approximately 30% of organic compounds are believed to exhibit polymorphism (Zell, et al., Tetrahedron 56(36)6603-16 (2000)). Polymorphism is important in the formulation of pharmaceuticals, pigments and dyes, sweeteners, explosives, and agrochemicals. Polymorphism may cause physical properties such as density, melting point, and rate of dissolution to change.

Amorphous, as used herein, describes a non-crystalline solid material. The amorphous form of rebaudioside A (Form 4) has an improved rate of dissolution as compared to the polymorphic forms of rebaudioside A (Forms 1, 2, or 3). Those of ordinary skill in the art should appreciate that the rate of dissolution of a sweetener composition may be important in the formulation of solid and liquid sweetenable compositions, non-limiting examples of which include chewing gum, baked goods, and beverages.

The material properties of the three rebaudioside A polymorphs and the rebaudioside A amorphous form are summarized in the following table:

TABLE 1

Rebaudioside A Polymorph and Amorphous Forms

| | Form 1 Polymorph | Form 2 Polymorph | Form 3 Polymorph | Form 4 Amorphous |
|---|---|---|---|---|
| Rate of dissolution in H2O at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 1-3% | <0.05% |
| Moisture content | >5% | <1% | <3% | <6% |

The above-described material properties are only illustrative of particular embodiments of the polymorphic and amorphous forms of rebaudioside A. Those of ordinary skill in the art should appreciate that the anhydrous rebaudioside A polymorph (Form 2), rebaudioside A solvate polymorph, and amorphous rebaudioside A are hygroscopic and may absorb moisture to an amount up to about 10% by weight on a dry basis. Not wishing to be bound by any theory, it is believed that the methods described herein generally produce the anhydrous rebaudioside A polymorph (Form 2) and/or amorphous rebaudioside A composition (Form 4).

Figure 1:
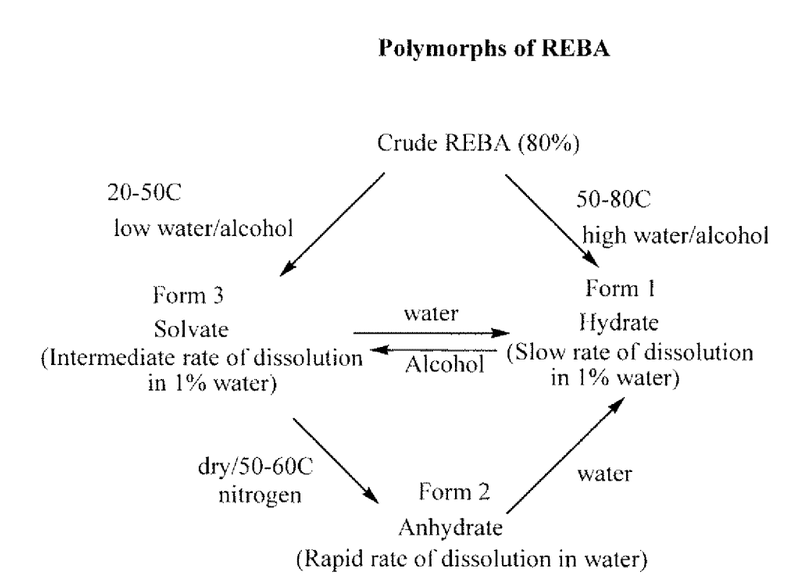
FIG. 1 is a schematic of the formation and conversion of rebaudioside A polymorphic and amorphous forms of rebaudioside A in accordance with an embodiment of this invention.

As illustrated in FIG. 1, the type of polymorphous or amorphous form produced may be dependent on the factors such as the composition of the aqueous organic solution, the temperature of the crystallization step, and the temperature during the drying step. Not wishing to be bound by any theory, Form 1 and Form 3 are believed to be formed during the single crystallization step while Form 2 is believed to be formed during the drying step after conversion from Form 1 and Form 3.

Low temperatures during the crystallization step, in the range of about 20° C. to about 50° C., and a low ratio of water to the organic solvent in the aqueous organic solvent results in the formation of Form 3. High temperatures during the crystallization step, in the range of about 50° C. to about 80° C., and a high ratio of water to the organic solvent in the aqueous organic solvent results in the formation of the Form 1. Form 1 can be converted to Form 3 by slurrying in an anhydrous solvent at about room temperature for about 2 to about 16 hours or by slurrying in an anhydrous solvent at about reflux temperature for about 0.5 to about 3 hours. Form 3 can be converted to Form 1 by slurrying the polymorph in water at about room temperature for approximately 16 hours or at about reflux temperature for about 2 to about 3 hours. Form 3 can be converted to the Form 2 during the drying process; however, increasing either the drying temperature above about 70° C. or the drying time of a substantially pure rebaudioside A composition can result in decomposition of the rebaudioside A and increase the remaining rebaudioside B impurity in the substantially pure rebaudioside A composition. Form 2 can be converted to Form 1 with the addition of water.

Form 4 may be obtained during the initial purification of rebaudioside A or directly from any individual polymorph or combination of polymorphs using methods well known to those of ordinary skill in the art. In addition, Form 4 may be obtained from a low purity rebaudioside A composition or a substantially pure rebaudioside A composition obtained through purification means other than those described hereinabove. Non-limiting examples of methods for preparing amorphous forms of rebaudioside A include ball milling, precipitation, lyophilization, cryogrinding, and spray-drying of a rebaudioside A composition.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, percentages (%'s) are by weight.

EXAMPLES

The purity of the rebaudioside A compositions described in the examples hereinbelow was determined using HPLC. Methods of performing HPLC analysis are well known to those of ordinary skill in the art. Briefly described, the HPLC analysis was performed using a ZORBAX $NH_2$ column (150× 4.6 mm, 5 μm) at a temperature of 30° C. The mobile phase comprised a solution of 20% buffer (0.0125% acetic, acid and 0.0125% ammonium acetate) and 80% acetonitrile at a flow rate of 1.5 mL/min. 12 μL of each sample was injected in duplicate and the sample was analyzed using a UV detector at 210 nm (4 nm bandwidth) with a reference of 260 nm (100 nm bandwidth). The HPLC analysis required a run time ranging from 40 to 60 min.

A buffer solution of 0.0125% acetic acid and 0.0125% ammonium acetate was prepared by dissolving 0.125 g ammonium acetate and 125 μL glacial acetic acid in one liter of water. The retention time of rebaudioside B was adjusted by varying the ratio of ammonium acetate to acetic acid while maintaining a total of 0.025% of both combined. Increasing the amount of acetic acid decreased the retention time of rebaudioside B.

The mobile phase was prepared by mixing the buffer solution with acetonitrile to achieve a rebaudioside A retention time of 7.0±0.5 min. Initially, this was approximately 20% buffer (200 mL of buffer and 800 mL of acetonitrile). Increasing the amount of acetonitrile by 1 to 2% increased the retention time of rebaudioside A by about one minute.

A diluent solution was prepared by mixing 750 mL of acetonitrile and 250 mL of the buffer solution. Rebaudioside A standards were prepared by diluting 20.0±0.5 mg (recorded to the nearest 0.1 mg) of the rebaudioside A standard with 4 mL of the diluent solution to make a standard solution of approximately 5000 mg/L. The rebaudioside A standard solution was injected at 10.8, 11.4, 12.6 and 13.2 μL. The moisture content was measured by Karl Fischer analysis every time a standard was prepared and corrections were made based on the solvent purity according to the certificate of analysis. Alternatively, rebaudioside A standards were prepared by diluting individual samples of 18, 19, 21 and 22 (each ±0.2) mg of rebaudioside A standard with 4 mL of the diluent solution (correcting for moisture and purity). The individually prepared samples were injected at the same level as the samples (12 μL).

Stevioside standards were prepared by diluting 12.5±0.5 mg (recorded to the nearest 0.1 mg) of the stevioside standard with 5 mL of the diluent solution to make a standard solution of approximately 2500 mg/L standard (stock A) (correcting for moisture and purity). The stevioside standard was then diluted using one mL of stock A to ten mL of diluent to produce a 250 mg/L standard (stock B), and stock standards were diluted to final concentrations ranging from 2.5 to 50 mg/L.

Samples of the rebaudioside A compositions were prepared by diluting 125±2 mg (recorded to the nearest 0.1 mg) of the rebaudioside A composition with 25 mL of the diluent solution to make a sample solution of approximately 5000 mg/L (correcting for moisture). If the samples were not analyzed immediately, they were stored without headspace, under nitrogen, and desiccated.

The following table provides a guideline for retention times (RT) for rebaudioside A and other steviol glycosides. However, those of ordinary skill in the art should appreciate that the retention times may be modified as needed.

TABLE 2

HPLC Retention Guidelines

| Compound | RT (min) |
|---|---|
| Stevioside | 4.53 |
| Rebaudioside C | 5.21 |
| Rebaudioside F | 5.62 |
| Rebaudioside A | 7.07 |
| Rebaudioside D | 15.79 |
| Steviolbioside | 18.35 |
| Rebaudioside B | 35.83 |

Low purity rebaudioside A compositions (having from 41-62% by weight rebaudioside A) were purified using a single crystallization step to obtain a substantially pure steviol glycoside composition having a high purity of rebaudioside A and high yield. Five different low purity rebaudioside A compositions were used having rebaudioside A purities from about 41% to about 62% by weight and total steviol glycoside content from about 88% to about 92% by weight (based on analytical HPLC analysis). The total amount of steviol glycosides in these examples was based on the combined amounts of rebaudioside A, rebaudioside B, rebaudioside C, rebaudioside D, rebaudioside F, stevioside, and steviolbioside.

Two of the low purity rebaudioside A compositions were obtained from Shenzhen (Shenzhen NII Natural Food Ingredients C., Ltd., China). Two of the low purity rebaudioside A compositions were obtained from Shandong (Shandong Huaxian Stevia Company, China). Still another of the low purity rebaudioside A compositions was obtained from Hailin (Hailin Farm, China). The amount of rebaudioside A and total steviol glycoside content in each of these compositions is set forth in Table 3 below.

TABLE 3

Summary of Low Purity Rebaudioside A Compositions

| Supplier | Amount of Rebaudioside A (% by weight) | Amount of Seven Steviol Glycosides (% by weight) | Amount of Nine Steviol Glycosides (% by weight) |
|---|---|---|---|
| Shenzhen (41%) | 41% | 90% | 93% |
| Shenzhen (62%) | 62% | 89% | 92% |
| Shandong (42%) | 42% | 88% | 92% |
| Shandong (51%) | 51% | 92% | 94% |
| Hailin | 56% | 88% | 91% |

Example Set A

Experimental conditions of the crystallization are summarized in Tables 4 and 5 and the results are summarized in Table 6.

The low purity rebaudioside A compositions (50 g) were combined with an organic solvent while stirring at a mixing temperature for a desired period of time to obtain a substantially clear solution. The solution was allowed to cool to room temperature (22° C.) and optionally was seeded with substantially pure rebaudioside A (>99.0%). Generally, precipitation was almost instantaneous upon cooling to room temperature. The precipitate was filtered and washed with either room temperature or cold ethanol (95%, 22° C. or 4° C.) and dried in a vacuum oven-desiccator at 50-60° C. for 2 to 4 days.

The amount of the resulting precipitate was determined and the precipitate was subjected to analytical HPLC (Agilent 1100) using the universal CAD (charged aerosol) detector to obtain a quantitative estimate of both the amount of rebaudioside A and the total amount of seven steviol glycosides (including rebaudioside A, rebaudioside B, rebaudioside C, stevioside, dulcoside A, rubusoside and Steviolbioside) and nine steviol glycosides (including rebaudioside A, rebaudioside B, rebaudioside C, rebaudioside D, rebaudioside F, stevioside, dulcoside A, rubusoside and Steviolbioside). The total mass yield and total rebaudioside A yield (both overall and relative to the total amount of rebaudioside A present in the low purity rebaudioside A compositions) then were determined. Example numbers 6, 7, 10, 11, 12, 15, 16, 25, 26, 27, 31, 32, 36, and 37 are described in more detail hereinbelow.

TABLE 4

Summary of Experimental Conditions

| Exp. No. | Solvent System* | Solvent (mL) | Mix Temperature (° C.) | Mix Time (min.) |
|---|---|---|---|---|
| 1 | A | 250 | 55 | 10 |
| 2 | B | 250 | 50 | 10 |
| 3 | C | 400 | 50 | 10 |
| 4 | D | 400 | 55-59 | 8 |
| 5 | E | 300 | 52-56 | 8 |
| 6 | D | 300 | 52 | 6 |
| 7 | D | 200 | 57 | 13 |
| 8 | F | 300 | 52 | 10 |
| 9 | D | 200 | 35-40 | 30 |
| 10 | G* | 210 | 35-40 | 30 |
| 11 | G* | 210 | 85 | 5-6 |
| 12 | A | 250 | 50 | 10 |
| 13 | B | 250 | 50 | 10 |
| 14 | C | 400 | 50 | 10 |
| 15 | D | 400 | 53 | 21 |
| 16 | D | 250 | 22 | 60 |
| 17 | A | 250 | 50 | 10 |
| 18 | B | 250 | 50 | 10 |
| 19 | C | 400 | 50 | 10 |
| 20 | D | 400 | 53-57 | 16 |
| 21 | E | 300 | 52 | 7 |
| 22 | D | 300 | 53 | 15 |
| 23 | D | 200 | 57 | 10 |
| 24 | F | 300 | 53 | 10 |
| 25 | D | 200 | 35-40 | 30 |
| 26 | G* | 210 | 35-40 | 30 |
| 27 | G* | 210 | 85 | 5-6 |
| 28 | A | 250 | 50 | 10 |
| 29 | B | 250 | 50 | 10 |
| 30 | C | 500 | 50 | 15 |
| 31 | D | 400 | 56 | 8 |
| 32 | G | 210 | 78 | 5-6 |
| 33 | A | 250 | 50 | 10 |
| 34 | B | 250 | 50 | 10 |
| 35 | C | 400 | 50 | 10 |
| 36 | D | 400 | 56 | 7.5 |
| 37 | H | 265 | 22 | 30 |

*Denotes methods in which solution of low purity rebaudioside A were seeded with substantially pure rebaudioside A (>99.0%) in an amount from about 0.0001% to about 0.001% by weight of the low purity rebaudioside A solution.

TABLE 5

Summary of Organic Solvent Systems

| Method | Solvent System |
|---|---|
| A | 4 parts ethanol (95%):1 part methanol |
| B | 1.5 parts ethanol (95%):1 part methanol |
| C | methanol (100%) |
| D | ethanol (95%) |
| E | methanol (95%) |
| F | ethyl acetate extraction + ethanol (95%) |
| G | 20 parts ethanol (95%):1 part water |
| H | 50 parts ethanol (95%):3 parts water |

TABLE 6

Summary of Experimental Results

| Exp. No. | Total Yield (% mass) | Total Reb A Yield (% mass) | Reb A Yield Relative to Reb A in crude (% mass) | Total 7 Steviol Glycosides (% mass) | Total 9 Steviol Glycosides (% mass) | Reb A (% mass) |
|---|---|---|---|---|---|---|
| 1 | 75.30 | 31.63 | 77 | 91 | 94 | 42 |
| 2 | 80.20 | 34.49 | 84 | 93 | 95 | 43 |
| 3 | 56.70 | 25.52 | 62 | 95 | 97 | 45 |
| 4 | 24.60 | 18.45 | 45 | 95 | 97 | 75 |
| 5 | 73.85 | 32.49 | 79 | 92 | 95 | 44 |
| 6 | 34.90 | 28.27 | 69 | 93 | 95 | 81 |
| 7 | 36.34 | 28.71 | 70 | 94 | 96 | 79 |
| 8 | 35.91 | 25.86 | 63 | 92 | 95 | 72 |
| 9 | 34.52 | 27.27 | 67 | 93 | 96 | 79 |
| 10 | 24.60 | 23.86 | 58 | 96 | 98 | 97 |
| 11 | 25.94 | 23.35 | 57 | 95 | 98 | 90 |
| 12 | 59.17 | 47.93 | 77 | 93 | 97 | 81 |
| 13 | 73.50 | 49.25 | 79 | 93 | 96 | 67 |
| 14 | 66.20 | 47.66 | 77 | 93 | 96 | 72 |
| 15 | 53.87 | 47.94 | 77 | 94 | 97 | 89 |
| 16 | 53.20 | 49.48 | 80 | 95 | 98 | 93 |
| 17 | 68.80 | 31.65 | 75 | 91 | 95 | 46 |
| 18 | 73.60 | 33.12 | 79 | 92 | 95 | 45 |
| 19 | 59.60 | 27.42 | 65 | 98 | 98 | 46 |
| 20 | 31.67 | 22.49 | 54 | 91 | 95 | 71 |
| 21 | 64.47 | 25.14 | 60 | 86 | 91 | 39 |
| 22 | 40.04 | 26.83 | 64 | 89 | 94 | 67 |
| 23 | 42.73 | 27.77 | 66 | 90 | 94 | 65 |
| 24 | 37.67 | 27.88 | 66 | 90 | 94 | 74 |
| 25 | 47.00 | 28.67 | 68 | 89 | 94 | 61 |
| 26 | 28.60 | 23.74 | 57 | 92 | 96 | 83 |
| 27 | 23.12 | 21.04 | 50 | 92 | 97 | 91 |
| 28 | 69.66 | 38.31 | 75 | 94 | 97 | 55 |
| 29 | 77.10 | 41.63 | 82 | 95 | 97 | 54 |
| 30 | 52.50 | 28.88 | 57 | 98 | 98 | 55 |
| 31 | 53.18 | 42.01 | 82 | 95 | 97 | 79 |
| 32 | 35.82 | 34.39 | 67 | 97 | 99 | 96 |
| 33 | 64.60 | 28.42 | 62 | 87 | 91 | 44 |
| 34 | 71.20 | 32.75 | 71 | 88 | 92 | 46 |
| 35 | 67.60 | 34.48 | 75 | 93 | 96 | 51 |
| 36 | 37.28 | 28.71 | 62 | 92 | 96 | 77 |
| 37 | 26.40 | 23.76 | 52 | 93 | 96 | 90 |

Example 6

Low purity rebaudioside A composition (50 g, 41%) was combined with 300 mL of ethanol (95%) and heated to 52° C. for 6 minutes while stirring. The solution was cooled and left at room temperature (22° C.) for three days while stirring. The precipitate was filtered, washed with ethanol (5-10 mL 95%, 22° C.), and dried for two days in a vacuum oven-desiccator (50° C.) to obtain 17.45 g of a steviol glycoside composition (34.90% yield) having 81% rebaudioside A and 95% total steviol glycosides.

Example 7

Low purity rebaudioside A composition (50 g, 41%) was combined with 200 mL of ethanol (95%) and heated to 57° C. for 13 minutes while stirring. The solution was cooled and left at room temperature (22° C.) for four days while stirring. The precipitate was filtered, washed with ethanol (5-10 mL 95%, 22° C.), and dried for two days in a vacuum oven-desiccator (50° C.) to obtain 18.17 g of a steviol glycoside composition (36.34% yield) having 79% rebaudioside A and 96% total steviol glycosides.

Example 10

Low purity rebaudioside A composition (50 g, 41%) was combined with 200 mL of ethanol (95%) and 10 ml, water and heated to 35-40° C. for 30 minutes while stirring. The solution was cooled and then seeded with substantially pure rebaudioside A (+99.0%) at room temperature (22° C.) and allowed to sit for one day at room temperature, for one day at 4° C., and again for one day at room temperature. The precipitate was filtered, washed with ethanol (3×10 mL 95%, 4° C.), and dried for two days in a vacuum oven-desiccator (50° C.) to obtain 12.3 g of a steviol glycoside composition (24.6% yield) having 97% rebaudioside A and 98% total steviol glycosides.

Example 11

Low purity rebaudioside A composition (50 g, 41%) was combined with 200 mL of ethanol (95%) and 10 mL water, fitted with a cold water reflux condenser, and heated in a water bath at 85° C. for 5-6 minutes while stirring. The solution was cooled and then seeded with substantially pure rebaudioside A (+99.0%) at room temperature (22° C.) and left at room temperature for three days while stirring. The precipitate was filtered and washed with ethanol (3×10 mL 95%, 4° C.) on the fourth day and dried for two days in a vacuum oven-desiccator (60° C.) to obtain 12.97 g of a steviol glycoside composition (25.94% yield) having 90% rebaudioside A and 98% total steviol glycosides.

Example 12

Low purity rebaudioside A composition (50 g, 62%) was combined with 200 mL of ethanol (95%) and 50 mL of methanol (100%) and heated to 50° C. for 10 minutes while stirring. The solution was cooled and left at room temperature (22° C.) overnight while stirring. The precipitate was filtered, washed with ethanol (2×30 mL 95%, 22° C.), and dried for two days in a vacuum oven-desiccator (50° C.) to obtain 29.58 g of a steviol glycoside composition (59.17% yield) having 81% rebaudioside A and 97% total steviol glycosides.

Example 15

Low purity rebaudioside A composition (50 g, 62%) was combined with 400 mL of ethanol (95%) and heated to 53° C. for 21 minutes while stirring. The solution was cooled and left at room temperature (22° C.) overnight while stirring. The precipitate was filtered, washed with ethanol (10-15 mL 95%, 22° C.), and dried for two days in a vacuum oven-desiccator (50° C.) to obtain 26.93 g of a steviol glycoside composition (53.87% yield) having 89% rebaudioside A and 97% total steviol glycosides.

Example 16

Low purity rebaudioside A composition (50 g, 62%) was combined with 250 mL of ethanol (95%) at room temperature (22° C.) for 60 minutes while stirring. The solution was left at room temperature overnight while stirring. The precipitate was filtered, washed with ethanol (10-15 mL 95%, 22° C.), and dried for two days in a vacuum oven-desiccator (60° C.) to obtain 26.6 g of a steviol glycoside composition (53.2% yield) having 93% rebaudioside A and 98% total steviol glycosides.

Example 24

Low purity rebaudioside A composition (50 g, 42%) was combined with 150 mL of ethyl acetate at room temperature (22° C.) for 15 minutes while stirring. The precipitate was filtered and then re-suspended in 300 mL of ethanol (95%) and heated to 52° C. for 10 minutes while stirring. The solution was cooled and left at room temperature (22° C.) for four days while stirring. The precipitate was filtered, washed with ethanol (5-10 mL 95%, 22° C.), and dried for two days in a vacuum oven-desiccator (50° C.) to obtain 18.83 g of a steviol glycoside composition (37.67% yield) having 74% rebaudioside A and 94% total steviol glycosides.

Example 26

Low purity rebaudioside A composition (50 g, 42%) was combined with 200 ml of ethanol (95%) and 10 mL of water and heated to 35-40° C. for 30 minutes while stirring. The solution was cooled and then seeded with substantially pure rebaudioside A (+99.0%) at room temperature (22° C.) and left undisturbed at room temperature for one day and at 4° C. for one day. The precipitate was filtered, washed with ethanol (3×10 mL 95%, 4° C.), and dried for two days in a vacuum oven-desiccator (50° C.) to obtain 14.3 g of a steviol glycoside composition (28.6% yield) having 97% rebaudioside A and 98% total steviol glycosides.

Example 27

Low purity rebaudioside A composition (50 g, 42%) was combined with 200 mL of ethanol (95%) and 10 mL water, fitted with a cold water reflux condenser, and heated in a water bath at 85° C. for 5-6 minutes while stirring. The solution was cooled and then seeded with substantially pure rebaudioside A (+99.0%) at room temperature (22° C.) and left at room temperature for three days while stirring. The precipitate was filtered and washed with ethanol (3×10 mL 95%, 4° C.) on the fourth day and dried for two days in a vacuum oven-desiccator (60° C.) to obtain 11.56 g of a steviol glycoside composition (23.12% yield) having 91% rebaudioside A and 97% total steviol glycosides.

Example 31

Low purity rebaudioside A composition (50 g, 51%) was combined with 400 mL of ethanol (95%) at heated to 56° C. for 8 minutes while stirring. The solution was cooled and left at room temperature (22° C.) overnight while stirring. The precipitate was filtered, washed with ethanol (10-15 mL 95%, 22° C.), and dried for two days in a vacuum oven-desiccator (50° C.) to obtain 26.59 g of a steviol glycoside composition (53.18% yield) having 79% rebaudioside A and 97% total steviol glycosides.

Example 32

Low purity rebaudioside A composition (50 g, 51%) was combined with 200 mL of ethanol (95%) and 10 ml, water, fitted with a cold water reflux condenser, and heated in a water bath at 78° C. for 6-8 minutes while stirring. The solution was cooled and left at room temperature (22° C.) overnight while stirring. The precipitate was filtered and washed with ethanol (3×10 mL 95%, 4° C.) and dried for four days in a vacuum oven-desiccator (60° C.) to obtain 17.91 g of a steviol glycoside composition (35.82% yield) having 96% rebaudioside A and 99% total steviol glycosides.

Example 36

Low purity rebaudioside A composition (50 g, 46%) was combined with 400 mL of ethanol (95%) and heated to 56° C. for 7.5 minutes while stirring. The solution was cooled and left at room temperature (22° C.) for five days while stirring. The precipitate was filtered, washed with ethanol (10-15 mL 95%, 22° C.), and dried for two days in a vacuum oven-desiccator (50° C.) to obtain 18.64 g of a steviolglycoside composition (37.28% yield) having 77% rebaudioside A and 96% total steviolglycosides.

Example 37

Low purity rebaudioside A composition (50 g, 46%) was combined with 250 mL of ethanol (95%) and 15 ml of water at room temperature (22° C.) for 60 minutes while stirring. The solution was left at room temperature overnight while stirring. The precipitate was filtered, washed with ethanol (10-15 mL 95%, 22° C.), and dried for four days in a vacuum oven-desiccator (60° C.) to obtain 13.2 g of a steviolglycoside composition (26.40% yield) having 90% rebaudioside A and 96% total steviolglycosides.

Example Set B

A single step crystallization of a low purity rebaudioside A composition was conducted using various organic solvents and experimental conditions. The amount of the resulting precipitate was determined for each crystallization and the precipitate was subjected to analytical HPLC (Agilent 1100) using the universal CAD (charged aerosol) detector to obtain a quantitative estimate of the amount of rebaudioside A in the resulting composition. The total mass yield and total rebaudioside A yield (both overall and relative to the total amount of rebaudioside A present in the low purity rebaudioside A compositions) then were determined. The results are summarized in Table 7 and experimental conditions described in detail hereinbelow.

TABLE 7

Summary of Experimental Results

| Exp. No. | Starting Mass (g) | Starting Reb A Purity (% mass) | Final Mass (g) | Total Yield (% mass) | Final Reb A Purity (% mass) | Reb A Yield Relative to Reb A in crude (% mass) |
|---|---|---|---|---|---|---|
| 1 | 5.0 | 62 | 2.15 | 43.00 | 92.5 | 64.15 |
| 2 | 5.0 | 62 | 2.20 | 44.00 | 94.96 | 67.39 |
| 3 | 5.0 | 62 | 2.55 | 51.00 | 96.3 | 79.21 |
| 4 | 5.0 | 62 | 3.25 | 65.00 | 87 | 91.21 |
| 5 | 5.0 | 62 | 3.32 | 66.40 | 77.6 | 83.11 |
| 6 | 5.0 | 41 | 1.87 | 37.40 | 81 | 73.89 |
| 7 | 5.0 | 41 | 1.65 | 33.00 | 81.62 | 65.69 |
| 8 | 10.0 | 62 | 5.85 | 58.50 | 90.6 | 85.49 |
| 9 | 10.0 | 46 | 4.40 | 44.00 | 73 | 69.83 |
| 10 | 5.0 | 51 | 2.60 | 52.00 | 84.72 | 86.38 |
| 11 | 5.0 | 46 | 2.24 | 44.80 | 78 | 75.97 |
| 12 | 5.0 | 62 | 2.30 | 46.00 | 83.46 | 61.92 |
| 13 | 5.0 | 41 | 1.85 | 37.00 | 80 | 72.20 |
| 14 | 5.0 | 54 | 1.85 | 37.00 | 88 | 60.30 |
| 15 | 5.0 | 43 | 1.36 | 27.20 | 85.82 | 54.29 |

Example 1

A low purity rebaudioside A composition (5 g, 62%) was combined with 40 mL of ethanol (90%) and heated to 45 to 58° C. for 20 minutes. The solution was filtered while hot to remove a trace amount of insoluble. The filtrate was cooled and left at room temperature (22° C.) for 44 hours while stirring. The precipitate was filtered, washed with absolute ethanol (22° C.), and dried for 24 hours to obtain 2.15 g of a steviol glycoside composition (43% yield) having 92.5% rebaudioside A.

Example 2

A low purity rebaudioside A composition (5 g, 62%) was combined with 20 mL of ethanol (90%) and heated to 45 to 58° C. for 20 minutes. The solution was filtered while hot to remove a trace amount of insoluble. The filtrate was cooled and left at room temperature (22° C.) for 44 hours while stirring. The precipitate was filtered, washed with aqueous ethanol (70%, −5° C.), and dried for 24 hours at 65° C. under vacuum over dririte to obtain 2.2 g of a steviol glycoside composition (44% yield) having 94.96% rebaudioside A.

Example 3

A low purity rebaudioside A composition (5 g, 62%) was combined with 20 mL of ethanol (95%) and heated to 45 to 50° C. for 20 minutes. The solution was filtered while hot to remove a trace amount of insoluble. The filtrate was cooled and left at room temperature (22° C.) for 44 hours and at 5° C. for 1 hour while stirring. The precipitate was filtered, washed with absolute ethanol (0° C.), and dried for 24 hours at 65° C. under vacuum over dririte to obtain 2.55 g of a steviol glycoside composition (51% yield) having 96.3% rebaudioside A.

Example 4

A low purity rebaudioside A composition (5 g, 62%) was combined with 20 mL of ethanol (95%) and 0.35 mL of water and stirred at room temperature (22° C.) for 2 days. The solution was cooled to 0 to 5° C. and left at this temperature for four hours while stirring. The precipitate was filtered, washed with aqueous ethanol (95%, 0° C.), and dried for 24 hours at 60° C. under vacuum to obtain 3.25 g of a steviol glycoside composition (65% yield) having 87% rebaudioside A.

Example 5

A low purity rebaudioside A composition (5 g, 62%) was combined with 20 mL of absolute ethanol and 1.0 mL of methanol and stirred at room temperature (22° C.) for 2 days. The solution was cooled to 0 to 5° C. and left at this temperature for four hours while stirring. The precipitate was filtered, washed with absolute ethanol (0° C.), and dried for 20 hours at 60° C. under vacuum to obtain 3.32 g of a steviol glycoside composition (66.4% yield) having 77.6% rebaudioside A.

Example 6

A low purity rebaudioside A composition (5 g, 41%) was combined with 20 mL of aqueous ethanol (95%, 22° C.). The solution was seeded with substantially pure rebaudioside A (>99.0%) at room temperature (22° C.) for 17 hours while stirring. The solution was cooled to 0 to 5° C. and left at this temperature for four hours while stirring. The precipitate was filtered, washed with aqueous ethanol (95%, 0° C.), and dried for 48 hours at 60° C. under vacuum to obtain 1.87 g of a steviol glycoside composition (37.2% yield) having 81.0% rebaudioside A.

Example 7

A low purity rebaudioside A composition (5 g, 41%) was combined with 20 mL of aqueous ethanol (90%, 22° C.). The solution was seeded with substantially pure rebaudioside A (>99.0%) at room temperature (22° C.) for 72 hours while stirring. The precipitate was filtered and dried for 24 hours at 60° C. under vacuum to obtain 1.65 g of a steviol glycoside composition (33% yield) having 81.62% rebaudioside A.

Example 8

A low purity rebaudioside A composition (10 g, 62%) was combined with 59.4 mL of aqueous ethanol (95%, 22° C.) and 0.6 mL of water at room temperature (22° C.). The solution was seeded with substantially pure rebaudioside A (>99.0%) at room temperature (22° C.) for 2 days while stirring. The precipitate was filtered, washed with aqueous ethanol (95%, 4° C.), and dried for 24 hours at 60° C. under vacuum to obtain 5.82 g of a steviol glycoside composition (58.2% yield) having 90.6% rebaudioside A.

Example 9

A low purity rebaudioside A composition (10.0 g, 46%) was combined with 30 mL of aqueous ethanol (95%, 22° C.) at room temperature (22° C.). The solution was seeded with substantially pure rebaudioside A (>99.0%) at room temperature (22° C.) for 2 days while stirring. The precipitate was filtered, washed with aqueous ethanol (95%, 5° C.), and dried for 24 hours at 60° C. under vacuum to obtain 4.4 g of a steviol glycoside composition (44% yield) having 73% rebaudioside A.

Example 10

A low purity rebaudioside A composition (5.0 g, 51%) was combined with 12.5 mL of aqueous ethanol (90%, 22° C.) at room temperature (22° C.). The solution was seeded with substantially pure rebaudioside A (>99.0%) at room temperature (22° C.) for 18 hours while stirring. The solution was cooled to 0 to 5° C. and left at this temperature for three hours while stirring. The precipitate was filtered and dried for 20 hours at 60° C. under vacuum to obtain 2.6 g of a steviol glycoside composition (52% yield) having 84.72% rebaudioside A.

Example 11

A low purity rebaudioside A composition (5.0 g, 46%) was combined with 12.5 mL of aqueous ethanol (90%, 22° C.) at room temperature (22° C.). The solution was seeded with substantially pure rebaudioside A (>99.0%) at room temperature (22° C.) for 24 hours while stirring. The solution was cooled to 0 to 5° C. and left at this temperature for four hours while stirring. The precipitate was filtered and dried for 24 hours at 60° C. under vacuum to obtain 2.24 g of a steviol glycoside composition (45% yield) having 78% rebaudioside A.

Example 12

A low purity rebaudioside A composition (5.0 g, 62%) was combined with 25 mL, of aqueous ethanol (95%, 22° C.) at room temperature (22° C.) for 15 minutes. The solution was seeded with substantially pure rebaudioside A (>99.0%) at room temperature (22° C.) for 24 hours while stirring. The precipitate was filtered, washed with aqueous ethanol, and dried for 24 hours at 60° C. under vacuum to obtain 2.3 g of a steviol glycoside composition (46% yield) having 83.46% rebaudioside A.

Example 13

A low purity rebaudioside A composition (5.0 g, 41%) was combined with 25 mL of aqueous ethanol (95%, 22° C.) at room temperature (22° C.). The solution was seeded with substantially pure rebaudioside A (>99.0%) at room temperature (22° C.) for 48 hours while stirring. The precipitate was filtered, washed with absolute ethanol (4° C.), and dried for 24 hours at 60° C. under vacuum to obtain 1.85 g of a steviol glycoside composition (37% yield) having 80.0% rebaudioside A.

Example 14

A low purity rebaudioside A composition (5.0 g, 51%) was combined with 20 mL of aqueous ethanol (95%, 22° C.) and 0.1 mL of water at room temperature (22° C.). The solution was seeded with substantially pure rebaudioside A (>99.0%) at room temperature (22° C.) for 24 hours while stirring. The precipitate was filtered and dried for 24 hours at 60° C. under vacuum to obtain 1.85 g of a steviol glycoside composition (37% yield) having 88.0% rebaudioside A.

Example 15

A low purity rebaudioside A composition (5.0 g, 43%) was combined with 20 of aqueous ethanol (95%, 22° C.) and 0.1 mL of water at room temperature (22° C.). The solution was seeded with substantially pure rebaudioside A (>99.0%) at room temperature (22° C.) for 72 hours while stirring. The precipitate was filtered, washed with aqueous ethanol (95%), and dried for 24 hours at 60° C. under vacuum to obtain 1.36 g of a steviol glycoside composition (27% yield) having 85.82% rebaudioside A.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A method for purifying a low purity rebaudioside A composition comprising the steps of:
    combining a low purity rebaudioside A composition with an aqueous organic solvent to form a low purity rebaudioside A solution, the low purity rebaudioside A composition containing rebaudioside A in a purity from 40% to 60% by weight on a dry basis, the aqueous organic solvent comprising water, in an amount from 5% to 10% water by weight, and ethanol;
    heating the low purity rebaudioside A solution at a temperature in a range from 35° C. to 40° C.;
    optionally seeding the rebaudioside A solution at an appropriate temperature with an amount of rebaudioside A sufficient to promote crystallization of rebaudioside A;
    crystallizing from the low purity rebaudioside A solution in a single step a substantially pure steviol glycoside composition comprising rebaudioside A and one or more other steviol glycosides selected from the group consisting of rebaudioside B, rebaudioside C, rebaudioside D, rebaudioside E, rebaudioside F, stevioside, dulcoside A, rubusoside, and steviolbioside; and
    separating and washing the substantially pure steviol glycoside composition;
    wherein the rebaudioside A is present in the substantially pure steviol glycoside composition in an amount greater than 95% by weight on a dry basis, and
    wherein the mass yield of the rebaudioside A is greater than 20% by weight and the mass yield of the steviol glycosides is greater than 25% by weight.

2. The method of claim 1, wherein rebaudioside A solution in the single crystallization step is stirred or unstirred.

3. The method of claim 1, wherein the rebaudioside A solution is heated for a period of time from about 5 to about 60 minutes.

4. The method of claim 1, wherein the crystallization of the steviol glycosides is allowed to continue for a period of time from about 0.5 hours to about 120 hours.

5. The method of claim 1, wherein the aqueous organic solvent and the crude rebaudioside A are present in the rebaudioside A solution in a weight ratio from about 4 to about 10 parts aqueous organic solvent to about 1 part crude rebaudioside A.

6. The method of claim 1, wherein the aqueous organic solvent further comprises a solvent selected from the group consisting of acetone, acetonitrile, methanol, 1-propanol, isopropanol, 1-butanol, 2-butanol, tert-butanol, and mixtures thereof.

7. The method of claim 1, wherein the aqueous organic solvent further comprises methanol.

8. The method of claim 7, wherein the ethanol and methanol are present in a weight ratio from about 20 parts to about 1 part ethanol to about 1 part methanol.

9. The method of claim 7, wherein the ethanol and methanol are present in a weight ratio from about 3 parts to about 1 part ethanol to about 1 part methanol.

10. The method of claim 1, further comprising cooling the rebaudioside A solution after the heating step.

11. The method of claim 1, wherein the rebaudioside A solution is seeded with an amount of rebaudioside A sufficient to promote crystallization of rebaudioside A.

12. The method of claim 1, further comprising drying the substantially pure steviol glycoside composition after washing the substantially pure steviol glycoside composition.

13. The method of claim 1, wherein the substantially pure mixture of steviol glycosides comprises no more than 2% of steviolbioside.

* * * * *